United States Patent [19]

Finke et al.

[11] Patent Number: 5,391,819
[45] Date of Patent: Feb. 21, 1995

[54] PROCESS OF MAKING CHIRAL 2-ARYL-1,4-BUTANEDIAMINE DERIVATIVES AS USEFUL NEUROKININ-A ANTAGONISTS

[75] Inventors: Paul E. Finke, Milltown; Jeffrey J. Hale, Westfield; Malcolm Maccoss, Freehold; Sander G. Mills, Woodbridge, all of N.J.

[73] Assignee: Merck & Co., Inc., Rahway, N.J.

[21] Appl. No.: 954,215

[22] Filed: Sep. 30, 1992

[51] Int. Cl.$^6$ ................................ C07C 59/40
[52] U.S. Cl. .................... 562/496; 562/490; 562/495; 562/840; 562/887; 544/334; 544/335; 544/336; 544/264; 546/147; 546/174; 546/341; 548/201; 548/206; 548/240; 548/341.5; 548/309.4; 548/376.1; 548/491; 549/71; 549/58; 549/469; 549/470; 549/499; 564/161
[58] Field of Search ............ 562/496, 490, 495, 840, 562/887; 544/334, 335, 336, 264; 546/147, 174, 341; 548/54, 201, 206, 240, 341.5, 309.4, 376.1, 491; 549/71, 469, 470, 499; 564/161

[56] References Cited

U.S. PATENT DOCUMENTS 4,904,656  2/1990  Weissmuller et al. ............ 514/231.5

FOREIGN PATENT DOCUMENTS 2029275  11/1990  Canada .
0428434  5/1991  European Pat. Off. .
0474561  3/1992  European Pat. Off. .
1178400  1/1970  United Kingdom .

OTHER PUBLICATIONS

CA 110(5), 38874r 1988.
Biochem. and Phy. Res. Comm. vol. 184, No. 3, (1992).
Beckwith, et al., Aust. J. Chem., 1992, 45, 289–308.

*Primary Examiner*—Paul J. Killos
*Attorney, Agent, or Firm*—Curtis C. Panzer; David L. Rose; Joseph F. DiPrima

[57] ABSTRACT

Disclosed herein is a process of making chiral 2-aryl-1,4-butanediamine derivatives useful as neurokinin-A antagonists of Formula 7

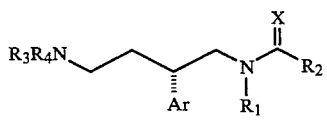

2 Claims, No Drawings

PROCESS OF MAKING CHIRAL 2-ARYL-1,4-BUTANEDIAMINE DERIVATIVES AS USEFUL NEUROKININ-A ANTAGONISTS

BACKGROUND OF THE INVENTION

The invention is directed to a process of making chiral 2-aryl-1,4-butanediamine derivatives useful as neurokinin-A antagonists. Compounds of the type including Sanofi SR 48968:

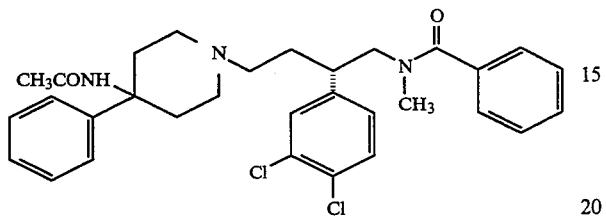

are disclosed in EP0 474 561 A1 published Mar. 11, 1992. Methods for making such compounds are disclosed in that application as well as EP 428 434 A2.

These references also teach the utility of such compounds as neurokinin-2 receptor antagonists useful in the treatment of certain respiratory, cardiovascular, CNS and antiinflammatory diseases. These references are hereby incorporated by reference.

DETAILED DESCRIPTION OF THE INVENTION

In one embodiment the invention concerns a process of making a compound of Formula 1

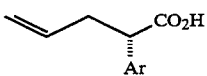    1 wherein:
Ar is:
a) $C_{6-10}$ aryl wherein the aryl is selected from the group consisting of
(1) phenyl,
(2) naphthyl,
(3) pyridyl,
(4) furyl,
(5) thienyl,
(6) thiazolyl,
(7) isothiazolyl,
(8) imidazolyl,
(9) benzimidazolyl,
(10) pyrazinyl,
(11) pyrimidyl,
(12) quinolyl,
(13) isoquinolyl,
(14) benzofuryl,
(15) benzothienyl,
(16) pyrazolyl,
(17) indolyl,
(18) purinyl,
(19) isoxazolyl,
wherein the aryl may be optionally substituted with
(1) halogen, preferably chlorine or fluorine,
(2) $C_{1-3}$alkyl,
(3) trifluoromethyl,
(4) $C_{1-3}$alkoxy,
(5) hydroxy, or
(6) methylenedioxy;
comprising:
(a) sequentially contacting a compound of Formula A

    A

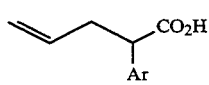

with a lithium base and an allyl halide in an inert solvent to yield a compound of Formula B

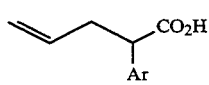    B

For purposes of this specification alkyl or alkenyl such as $C_{1-6}$ or $C_{1-6}$ alkenyl is understood to include both linear and branched claims.

For purposes of this specification the lithium base is defined to include lithium amides such as lithium bis(tri-$C_{1-4}$alkylsilyl)amide, including bis(trimethylsilyl)amide and lithium di-$C_{1-4}$alkylamide including diisopropylamide. Similarly, the inert solvent is intended to include diethyl ether, dimethoxyethane, di-n-butyl and diisopentyl ethers, anisole, cyclic ethers such as tetrahydropyran, 4-methyl-1,3-dioxane, dihydropyran, tetrahydrofurfuryl methyl ether, furan, and 2-ethoxytetrahydrofuran, as well as benzene, toluene, and xylene.

For purposes of this specification allyl halide is intended to include allyl chloride, iodide or bromide. The molar ratio of compound of Formula A to base should range from 2.0–2.5 to 1. The molar ratio of compound of Formula A to allyl halide should be 2.0–3.0 to 1. The reaction is conducted at −20° to 10° C. and is allowed to proceed until essentially completed in 30 to 120 minutes.

(b) resolving a compound of formula B to yield compound of formula 1 or 1a

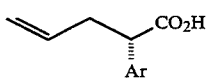    1

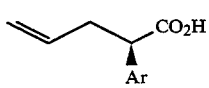    1a

The above resolution may be achieved, for example, by crystallization of the salt of compound B with a chiral organic amine, such as (1S)-phenylethylamine.

In an alternative embodiment, the invention concerns a process of making a compound of Formula 1 as defined above comprising:
(a) contacting a compound of Formula A

    A in an etheral solvent with tri$C_{1-4}$alkylacetyl halide and a tertiary amine to yield a compound of formula B′

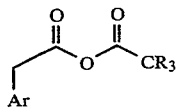

B'

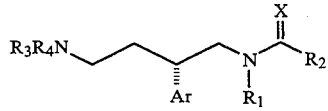

7

For purposes of this specification, triC$_{1-4}$alkylacetyl halide is intended to include alkyls methyl and ethyl, and chloride and bromide as the halide and the tertiary amine base is intended to include triethylamine, N,N-diisopropylethyl amine, and 4-methyl morpholine. The molar ratio of formula A to halide should be approximately 1.0–1.5 to 1. The molar ratio of A to tertiary amine 1–1.5 to 1. The reaction is allowed to proceed at from −20° to 0° C. until substantially complete.

(b) contacting a compound of formula B' with 3-lithio-(4S)-benzyl-2-oxazolidinone in an etheral solvent to yield a compound of formula 2.

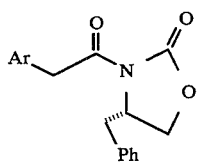

2

The molar ratio of formula B' to oxazolidinone should be approximately 1–1.5 to 1. The reaction is allowed to proceed at from −78° to 0° C. until substantially complete.

For purposes of this specification the lithium base is defined to include lithium amides such as lithium bis(tri-C$_{1-4}$alkylsilyl)amide, including bis(trimethylsilyl)amide and lithium di-C$_{1-4}$alkylamide including diisopropylamide. Similarly, the inert solvent is intended to include diethyl ether, dimethoxyethane, di-n-butyl and diisopentyl ethers, anisole, cyclic ethers such as tetrahydropyran, 4-methyl-1,3-dioxane, dihydropyran, tetrahydrofurfuryl methyl ether, furan, and 2-ethoxytetrahydrofuran, as well as toluene, benzene and xylene.

(C) Sequentially contacting a compound of Formula 2, with a strong base in an inert solvent and an allyl halide as defined above to yield a compound of Formula 3

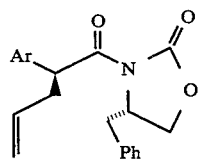

3 which upon saponification yields compound of Formula 1.

For purposes of this specification the strong base shall include alkali hydrides such as sodium or lithium hydride, and amides such as sodium or potassium bis(-trimethylsilyl)amide. The molar ratio of compound of Formula 2 to base should range from 1–1.5 to 1. The molar ratio of compound of Formula 2 to allyl halide should range from 2–10 to 1. The reaction is conducted at −78° to −20° C. and is allowed to proceed until essentially complete in from 30 to 120 minutes.

In a second embodiment the invention concerns a process of making a compound of Formula 7 wherein:
Ar is:
  a) C$_{6-10}$ aryl wherein the aryl is selected from the group consisting of
    (1) phenyl,
    (2) naphthyl,
    (3) pyridyl,
    (4) furyl,
    (5) thienyl,
    (6) thiazolyl,
    (7) isothiazolyl,
    (8) imidazolyl,
    (9) benzimidazolyl,
    (10) pyrazinyl,
    (11) pyrimidyl,
    (12) quinolyl,
    (13) isoquinolyl,
    (14) benzofuryl,
    (15) benzothienyl,
    (16) pyrazolyl,
    (17) indolyl,
    (18) purinyl,
    (19) isoxazolyl,
    wherein the aryl may be optionally substituted with
    (1) halogen, preferably chlorine or fluorine,
    (2) C$_{1-3}$alkyl,
    (3) trifluoromethyl,
    (4) C$_{1-3}$alkoxy,
    (5) hydroxy, or
    (6) methylenedioxy;
R$_1$ is:
  a) hydrogen, or
  b) C$_{1-6}$ alkyl,
R$_2$ is
  a) hydrogen,
  b) C$_{1-6}$ alkyl,
  c) C$_{2-6}$ alkenyl,
  d) Ar'-Y-, where Y is C$_{0-3}$alkyl and Ar' is selected from Ar defined previously,
  e) O—Z or NH—Z, where Z is C$_{1-6}$ alkyl,
R$_3$ and R$_4$ are each individually
  1) C$_1$ to C$_6$ alkyl,
  2) C$_1$ to C$_6$ alkenyl,
  3) Ar", where Ar" is selected from Ar as previously defined or R$_3$ and R$_4$ are joined together to form a saturated ring of 5 to 9 atoms:
  said ring having 1 or 2 heteroatoms
  said hetero atoms selected from N, O and S said ring including

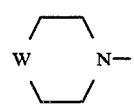

wherein W is
  1) C$_{0-5}$ alkyl,
  2) Ar''', where Ar''' is selected from Ar as defined previously
  3)

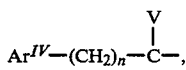

where $Ar^{IV}$ is phenyl, pyridyl, or thienyl; n is 0 or 1; and V is —OH, $C_{1-4}$ alkoxy, $C_{1-4}$ acyloxy, hydrogen, carboxy, $C_{1-4}$ carbalkoxy, cyano, —$N(R)_2$, —SR, or —NHCOR, where R is independently selected from hydrogen, and $C_{1-4}$ alkyl; and X is O or S; comprising:
(a) contacting a compound of Formula 1

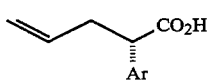

with a chlorinating agent in a halo carbon solvent to yield a compound of Formula 1'

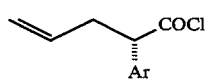

For purposes of this specification the chlorinating agent is defined to include oxalyl chloride or thionyl chloride or $PCl_5$. The halocarbon solvent is defined to include halo $C_{1-4}$ alkyl, including dichloromethane. The ratio of compound of Formula 1 to activating agent should range from 1-100 to 1. The reaction is conducted at 0° to 25° C. and is allowed to proceed until essentially complete in from 10 to 120 minutes.

(b) contacting a compound of Formula 1, with a primary $C_{1-4}$ alkyl amine in a chlorinated hydrocarbon, a hydrocarbon, or an etheral solvent to yield a compound of Formula 4

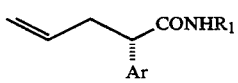

For purposes of this specification primary $C_{1-6}$ alkyl amine are defined to include methyl ethyl amine. The chlorinated hydrocarbon solvent is defined to include methylene chloride. The hydrocarbon solvent is defined to include toluene, xylene, and benzene as well as $C_{4-10}$ alkyl or $C_{4-10}$ alkenyl. The etheral solvent is defined to include as diethyl ether, dimethoxyethane, di-n-butyl and diisopentyl ethers, anisole, cyclic ethers such as tetrahydropyran, 4-methyl-1,3-dioxane, dihydropyran, tetrahydro-furfuryl methyl ether, furan and 2-ethoxytetrahydrofuran. The ratio of compound of Formula 1' to amine should be 1-100 to 1. The reaction is conducted at 0° to 25° C. and is allowed to proceed until essentially completed in 10 to 120 minutes.

(c) contacting a compound of Formula 4 in an aprotic solvent with a strong reducing agent, and thereafter an acylating agent to yield a compound of Formula 5

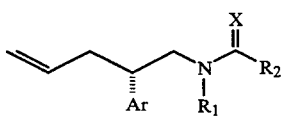

For purposes of this specification, the strong reducing agent shall be defined to include strong hydride reducing agents lithium aluminum hydride and diisobutylaluminum hydride. The aprotic solvent shall defined to include toluene, methylene chloride, xylene (otho, para, and meta), benzene, and hexanes. The acylating agent should be defined to include a $C_{1-6}$ acylchloride such as acetyl, propionyl or hexanoyl chloride, benzoyl chloride, phenylacetyl chloride; a $C_{1-6}$ alkyl haloformate such as methyl chloroformate, ethyl chloroformate or hexyl chloroformate; a $C_{1-6}$ alkyl isocyanate such as methyl, ethyl or hexyl isocyanate. The ratio of Formula 5 to reducing agent should be 1-10 to 1; and the ratio of Formula 5 to acylating agent should be 1-5 to 1. The reaction is allowed to proceed at from 0° to 100° C. until substantially complete in 1 to 24 hours.

(d) contacting a compound of Formula 5 with an oxidizing agent in a protic solvent to yield a compound of Formula 6.

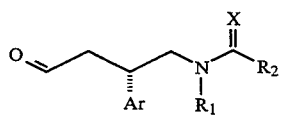

For purposes of this specification the oxidizing agent shall be defined to include a catalytic osmium tetroxide and sodium periodate, and ozone followed by reductive workup as with dimethylsulfide. The protic solvent shall be defined to include water, methanol, t-butanol. The ratio of compound of Formula 5 to oxidizing agent shall be 1-2 to 1. The reaction is allowed to proceed at 0° to 25° C. until substantially complete in 10 to 60 minutes.

(e) contacting a compound of Formula 6 with a secondary amine, and a reducing agent to yield a compound of Formula 7

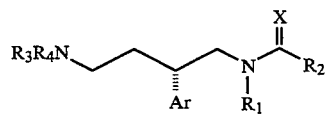

For purposes of the specification the secondary amine shall be defined to include dimethylamine, diethylamine pyrrolidine, piperidine, morpholine, and other groups as generically or specifically disclosed in Sanofi SR 48968 and EP 0 474 561, published Mar. 11, 1992, as well as EP 0 428 434. The reducing agent shall be defined to include sodium cyanoborohydride and sodium borohydride or a catalytic agent such as hydrogen and palladium on charcoal catalyst or hydrogen and Raney nickel catalyst. The ratio of Compound 6 to reducing agent shall be 1-5 to 1. The ratio of Formula 6 to amine shall be 1-2 to 1. The ratio of compound of Formula 6 to catalytic agent shall be 0.1-0.5 to 1. The reaction is allowed to proceed until substantially complete in 1 to 24 hours.

In an alternative embodiment, a compound of Formula 1 can be prepared by sequentially contacting a $C_{1-4}$alkyl phenylacetate with a lithium dialkyl or lithlim disilyl, as prevoiusly defined, and an allyl halide, as previously defined. Saponification of the resulting $C_{1-4}$alkyl. 2-aryl-4-pentenoate will afford a compound of Formula B which can be converted to a compound of Formula 1 as described above. The ratio of lithium dialkyl or disilylamide to $C_{1-4}$alkyl phenylacetate is approximately 1-1.2 to 1.

In an alternative embodiment the compound of Formula 1 can be converted to a compound of Formula 4 by contacting the compound of Formula 1 with an $C_{1-4}$ alkyl chloroformate, such as ethyl or isobutyl chloroformate in an etheral or aprotic solvent, as defined. above, with a tertiary amine such as tri $C_{1-4}$ alkylamine including triethylamine or $C_{1-4}$ alkyl morpholine such as 4-methylmorpholine followed by addition of a primary $C_{1-6}$alkyl amine as defined herein.

The ratio of Compound 1 to chloroformate shall be 1-1.5 to 1. The ratio of Compound 1 to tertiary amine shall be 1-1.5 to 1. The ratio of $C_{1-6}$alkylamine to Compound 1 shall be 1-5 to 1. The reaction is allowed to proceed at $-20°$ to $0°$ C. until substantially complete.

In an alternative embodiment the compound of Formula 1 can be converted to a compound of Formula 4 by contacting the compound of Formula 1 with dicyclohexacarbodiimide and 1-hydroxybenzotriazole; or 1-(3-dimethylaminopropyl-3-ethylcarbodiimide hydrochloride in an etheral or halo carbon solvent followed by addition of a primary $C_{1-6}$ alkylamine or arylamine.

The ratio of Compound 1 to dicyclohexacarbodiimide and 1-hydroxybenzotriazole; or 1-(3-dimethylaminopropyl-3-ethylcarbodiimide hydrochloride shall be 1.0-1.5 to 1. The ratio of $C_{1-6}$alkylamine to Compound 1 shall be 1-5 to 1. The reaction is allowed to proceed at $0°$ to $25°$ C. until substantially complete in from 10 to 60 minutes.

In an alternative embodiment, an allyl sulfonate can be substituted for the allyl halide in the preparation of Compound B from A and/or Compound 3 from 2.

The compounds of the present invention are prepared in a process that starts with an enantiomerically pure 2-aryl-4-pentenoic acid that is prepared by one of the two routes outlined in Scheme 1. Thus, in the first route, a substituted phenylacetic acid is first converted to its lithium dianion with a suitable base (for example, lithium bis(tri-methylsilyl)amide, lithium diisopropylamide) in an inert solvent (for example, tetrahydrofuran, dimethoxyethane) at low temperature. The dianion is then alkylated with an allyl halide (for example, chloride, bromide, iodide) to afford the racemic 2-aryl-4-pentenoic acid. The racemic acid is combined with a chiral organic amine (for example, 1-phenethylamine, brucine, cinchonidine) and fractional crystallization of the resulting diastereomeric salts from an appropriate solvent (for example, ethyl acetate, isopropanol, ethanol) gives one of the diastereomeric salts. Recovery of the acid is effected by partitioning the salt between a suitable organic solvent (for example, ethyl ether, ethyl acetate) and an aqueous solution of a mineral acid (for example, aqueous hydrochloric acid, aqueous sulfuric acid) to liberate the enantiomerically pure acid 1. Alternatively, resolution of the racemic 2-aryl-4-pentenoic acid can be effected by converting it to the ester or amide of a suitable organic alcohol or amine. The diastereomers thus obtained can be separated using chromatographic techniques commonly used by the synthetic organic chemist. The desired diastereomer is hydrolyzed with a heated solution of aqueous mineral acid to liberate the enantiomerically pure acid 1. The second route employs the Evans chiral oxazolidinone methodology (Evans, D. A.; Ennis, M. D.; Mathre, D. J. Journal of the American Chemical Society, 1982, 44, 5525). Thus, to prepare a (2S)-aryl-4-pentenoic acid, a substituted phenylacetic acid is first converted to the mixed anhydride with trimethylacetyl chloride, then reacted with 3-lithio-(4S)-benzyl-2-oxazolidinone (prepared from (4S)-benzyl-2-oxazolidinone and an organolithium compound, such as methyllithium or n-butyllithium) in a suitable inert solvent (for example, tetrahydrofuran, dimethoxyethane) to afford the acyl oxazolidinone 2. Acyl oxazolidinone 2 is then converted to its sodium enolate with a strong base (sodium bis(-trimethylsilyl)amide, sodium hydride) and alkylated with an allyl halide (chloride, bromide, iodide) in a suitable inert solvent (for example, tetra-hydrofuran, dimethoxyethane) to afford alkylated acyl oxazolidinone 3. Saponification of the alkylated acyl oxazolidinone 3 affords the (2S)-aryl-4-pentenoic acid 1. In alternative procedures, a substituted phenylacetyl chloride can replace the trimethylacetyl mixed anhydride ann any commonly used chiral oxazolidinone (for example, (4S)-isopropyl-2-oxazolidinone, (4S)-methyl-(5R)-phenyl-2-oxazolidinone) can be used to to form 2. For the preparation of a (2R)-aryl-4-pentenoic acid, the enantiomer of any of the aforementioned oxazolidinones can be used.

The process for the elaboration of the chiral 2-aryl-4-pentenoic acid 1 to the compounds of the present invention is outlined in Scheme 2. Thus, 1 is converted to the N-alkyl amide 4 by first activating 1 as the corresponding acid chloride (for example, by treating 1 with oxalyl chloride and catalytic N,N-dimethylformamide or thionyl chloride), mixed anhydride (for example, by treating 1 with an alkyl (ethyl, isobutyl) chloroformate and a tertiary amine base (for example, triethylamine, 4-methylmorpholine) in a suitable organic solvent (for example, dichloromethane, tetrahydrofuran) at low temperature), or activated ester (for example, by treating 1 with dicyclohexylcarbodiimide and 1-hydroxybenzotriazole or 1-(3-dimethyl-aminopropyl)-3-ethylcarbodiimide hydrochloride in a suitable solvent (for example, methylene, tetrahydrofuran)) and reacting activated 1 with a primary alkyl (for example, methyl, ethyl, benzyl) or aryl amine to give amide 4. Amide 4 is reduced with a strong hydride reducing agent (for example, lithium aluminum hydride, diisobutylaluminum hydride) to a secondary amine which is then acylated with an alkyl or aryl acid chloride, anhydride, chloroformate, or isocyanate to afford the N-alkyl-N-acyl-2-aryl-4-pentenamine 5. 5 is treated with an oxidizing agent (for example, catalytic osmium tetroxide and sodium periodate, ozone) in an appropriate solvent (for example, aqueous tetrahydrofuran, methylene chloride) to give the aldehyde 6. The aldehyde 6 is combined with a secondary amine and the resulting imine is reduced chemically (for example, sodium cyanoborohydride, sodium borohydride) or catalytically (for example, hydrogen and palladium on charcoal catalyst, hydrogen and Raney nickel catalyst) to afford the desired final compound 7.

Scheme 1

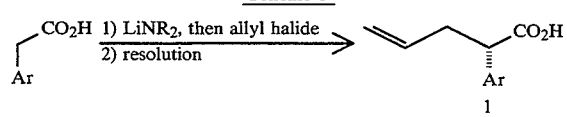

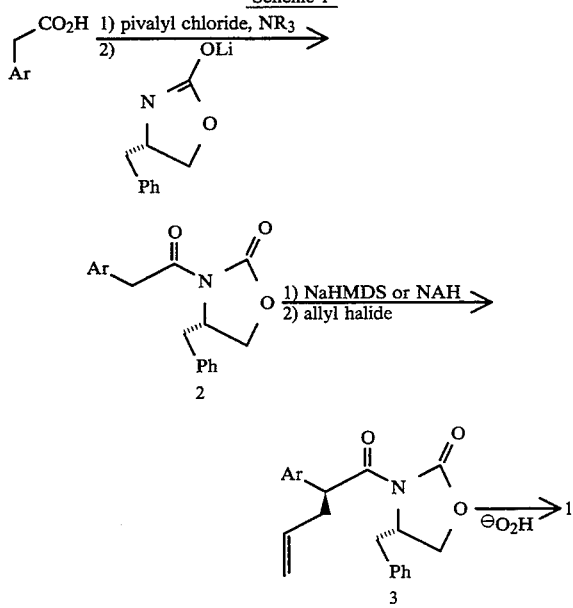

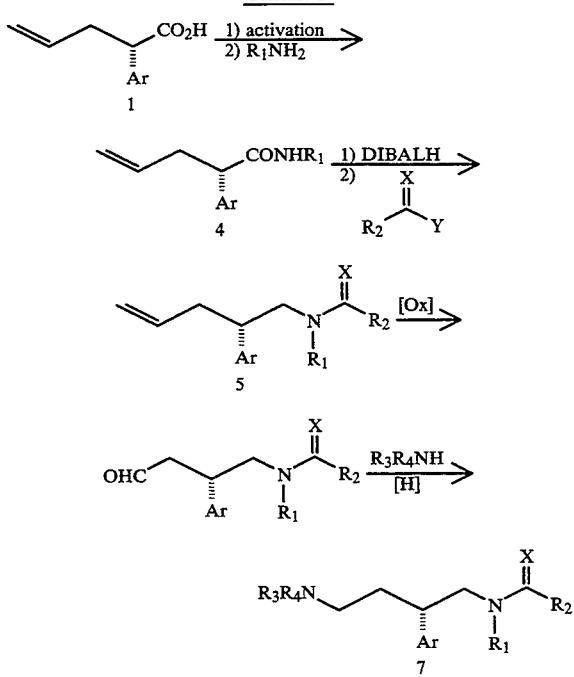

The Following Examples are intended to illustrate the invention and as such are not to be considered as limiting the Claims apended hereto. Starting materials are either generally available or their method of preparation are disclosed herein or are known. Reference may be made to Sanofi SR 48968, EP0 474 561 A1 published Mar. 11, 1992, and EP 428 434 A2 for these matters and the further use of the compounds produced by the processes disclosed herein.

General. Melting points (mp) were determined on a Thomas Hoover Capillary Melting Point Apparatus and are uncorrected. Specific rotations [a] were determined on a Perkin-Elmer Model 141 polarimeter at the sodium D line at 20° C. Proton and carbon-13 nuclear magnetic resonance (NMR) spectra were obtained with a Varian Associates XL-400 instrument on deuteriochloroform ($CDCl_3$) solutions unless otherwise specified. Chemical shifts are reported in parts per million downfield from tetramethylsilane internal reference. Multiplicities are reported as singlet (s), doublet (d), triplet (t), quartet (q), AB quartet (AB q), multipier (m), broad (br) and apparent (app). Coupling constants are in hertz. Infrared (IR) spectra were recorded on a Perkin-Elmer 1600 Series FT-IR instrument (selected absorption maxima are reported in cm $^{-1}$). Fast atom bombardment mass spectra (FAB-MS) were recorded on a Varian Associates MAT 731 or a Finnegan TSQ 70 spectrometer with dithiothreitol/dithioerythritol matrix. Elemental analyses were obtained from Robertson Laboratories (Madison, N.J.). EM Science Silica Gel 60 (230–400 mesh) was used for flash column chromatography (Still, W. C., Kahn, M., Mitra, A. Journal of Organic Chemistry, 1978, 52, 2273). Tetrahydrofuran (THF) was distilled from benzophenone ketyl; other solvents and reagents were obtained commercially and used as received unless otherwise specified. Aqueous solutions used include 2.0 $\underline{N}$ aqueous hydrochloric acid solution (2.0 $\underline{N}$ HCl), saturated aqueous ammonium chloride solution (sat'd $NH_4Cl$), saturated aqueous sodium bicarbonate solution (sat'd $NaHCO_3$), saturated aqueous sodium chloride solution (sat'd NACl), and 2.0 $\underline{N}$ aqueous sodium hydroxide solution (2.0 $\underline{N}$ NaOH). Organic solutions were dried over magnesium sulfate. All air-sensitive reactions were run under a nitrogen atmosphere.

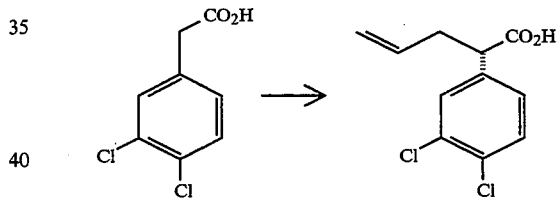

(2S)-(3,4-Dichlorophenyl)-4-pentenoic acid (1). A 1 L 3-necked flask, equipped with a thermometer, a 250 mL dropping funnel and a nitrogen inlet, was charged with a solution of 20.50 g (0.1 mol) of 3,4-dichlorophenylacetic acid in 100 mL of THF. The solution was cooled to −5° C. and 220 mL of 1$\underline{M}$ lithium bis(trimethylsilyl)amide in THF was added dropwise over a 30 min period, maintaining the temperature between −5° and 0° C. The resulting solution was stirred cold for 1.5 h and treated with a solution 20.6 mL (0.25 mol) of allyl bromide in 20 mL of THF. The resulting solution was stirred at 0° C. for 1 h. The reaction mixture was slowly poured into a mixture of 300 mL of ethyl ether, 50 mL of concentrated hydrochloric acid, and 200 g of ice. The layers were separated and the organic layer was washed with 400 mL of 2.0 $\underline{N}$ HCl, 400 mL of water, 400 mL of 5% aqueous sodium thiosulfate solution, 200 mL of sat'd NaCl, dried, and concentrated in vacuo. The crude product was dissolved in 200 mL of hexanes and cooled in a dry ice/acetone bath. The resulting solid was filtered and dried to afford 16.18 g of (±)-1. The filtrate was concentrated in vacuo and the residue was filtered through a pad of 250 g of silica gel using 4:1 v/v hexanes/ethyl acetate+1% acetic acid as the eluant to afford 8.26 g of (±)-1 (99% total yield).

A solution of 14.65 g (59.6 mmol) of (±)-1 in 150 mL of ethyl acetate was treated with 6.04 g (50.0 mmol) of (1S)-phenethylamine. A precipitate immediately formed; the mixture was warmed to dissolve all solids and the resulting solution was allowed to stand at rt for 5 h. The solid was filtered and dried (11.14 g). The solid was repeatedly (6 times) recrystallized from 100 mL of ethyl acetate for 24 h to afford 7.00 g of 1, (1S)-phenethylamine salt: [α]=+8.7 (c=1.1, CHCl$_3$).

The salt (6.75 g) was partitioned between 200 mL of ethyl ether and 50 mL of 2 N HCl. The layers were separated and the organic layer was washed with 50 mL of sat'd NaCl, dried, and concentrated in vacuo to afford 4.50 g of 1: [α]=+67.4 (c=1.0, CHCl$_3$), $^1$H NMR 2.46–2.54 (m, 1H), 2.76–2.83 (m, 1H), 3.61 (t, 1H, J=7.6), 5.03–5.11 (m, 2 H), 5.63–5.73 (m, 1H), 7.16 (dd, 1H, J=8.0, 2.6), 7.39–7.43 (m, 2H). Anal. Calcd for C$_{11}$H$_{10}$Cl$_2$O$_2$: C, 53.90; H, 4.11; Cl, 28.93. Found: C, 54.01; H, 4.03; Cl, 29.49.

3-(1-Oxo-2-(3,4-dichlorophenyl)ethyl-(4S)-benzyl-2-oxazolidinone (2). An oven-dried 1 L 3-necked flask, equipped with a thermometer, a septum and a nitrogen inlet, was charged with a Solution of 2.25 g (11.0 mmol) of 3,4-dichlorophenylacetic acid in 20 mL of THF. The solution was treated with 1.85 mL (13.3 mmol) of triethylamine and cooled to −10° C. Pivaloyl chloride (1.42 mL, 11.5 mmol) was added; the resulting slurry was stirred at −10° C. for 50 min and cooled to −78° C.

An oven-dried 100 mL flask, equipped with a septum, was flushed with nitrogen and charged with a solution of 1.77 g (10.0 mmol) of (4S)-benzyl-2-oxazolidinone in 20 mL of THF. The solution was stirred in a dry ice/acetone bath for 20 min and treated with 6.25 mL of 1.6 M n-butyllithium solution in hexanes. The resulting slurry was stirred cold for 20 min, then cannulated into the aforementioned mixed anhydride. The resulting mixture was stirred at −78° C. for 30 min, warmed to 0° C., and poured into 100 mL of ethyl ether and 100 mL of pH 7 phosphate buffer. The layers were separated; the organic layer was washed with 100 mL of sat'd NaHCO$_3$, 50 mL of sat'd NaCl, dried, and concentrated in vacuo. Flash chromatography on 140 g of silica gel using 3:1 v/v hexanes/ethyl ether as the eluant afforded 3.04 g (83%) of 2 as an oil:

$^1$H NMR 2.77 (dd, 1 H, J=13.2, 9.2), 3.26 (dd, 1H, J=13.2, 3.2), 4.20 and 4.30 (AB q, 2H, J=12.0), 4.21 and 4.23 (AB q, 2H, J=3.6), 4.65–4.71 (m, 1H), 7.13–7.19 (m, 3H), 7.26–7.33 (m, 4H); IR (neat) 1773, 1696. Anal. Calcd for C$_{18}$H$_{15}$Cl$_2$NO$_3$: C, 59.35; H, 4.15; N, 3.85; Cl, 19.47. Found: C, 59.06; H, 3.99; N, 3.71; Cl, 19.21.

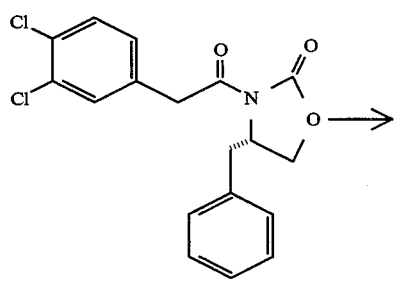

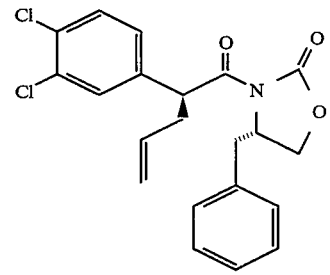

3-(1-Oxo-(2S)-(3,4-dichlorophenyl)-4-pentenyl)-(4S)-benzyl-2-oxazolidinone (3). A solution of 2.40 g (6.6 mmol) of 2 in 10 mL of THF was slowly added to 8.0 mL of sodium bis(trimethylsilyl)amide solution in THF at −78° C. After 15 min, 3.0 mL (30.1 mmol) of allyl iodide was added. The resulting mixture was warmed to −20° C. and stirred for 1 h. The reaction was quenched with 10 mL of sat'd NH$_4$Cl and partitioned between 50 mL of ethyl ether and 10 mL of water. The layers were separated; the organic layer was washed with 15 mL of 5% aqueous sodium thiosulfate solution, 15 mL of sat'd NaCl solution, dried and concentrated in vacuo. $^1$H NMR of the crude product showed it to be a 92:8 mixture of diastereomers. Flash chromatography on 150 g of silica gel using 9:1 v/v hexanes/ethyl ether as the eluant afforded 2.01 g (75%) of 3 as an oil: [α]=+102.2 (c=1.4, CHCl$_3$);

$^1$H NMR 2.48–2.55 (m, 1H), 2.76 (dd, 1H, J=13.6, 9.6), 2.86–2.94 (m, 1H), 3.32 (dd, 1H, J=13.6, 3.2), 4.08–4.15 (m, 2H), 4.59–4.65 (m, 1H), 5.04–5.16 (m, 2H), 5.70–5.80 (m, 1H), 7.21–7.39 (m, 7H), 7.50 (d, 1 H, J=2.0); IR (neat) 1779, 1697, 1386, 1364, 910, 732; FAB-MS 405(M+1)$^+$. Anal. Calcd for C$_{21}$H$_{19}$Cl$_2$NO$_3$: C, 62.38; H, 4.74; N, 3.46; Cl, 17.54. Found: C, 62.10; H, 4.49; N, 3.75; Cl, 17.37.

(2S)-(3,4-Dichlorophenyl)-4-pentenoic acid (1). A solution of 1.98 g (4.9 mmol) of 3 in 125 mL of 4:1 v/v THF/water at 0° C. was treated with 2.0 mL of 30% aqueous hydrogen peroxide solution and 250 mg (6.0 mmol) of lithium hydroxide monohydrate. The solution was stirred cold for 20 min, quenched with 2.0 g of sodium bisulfite, and partitioned between 50 mL of ethyl acetate and 50 mL of water. The layers were separated and the organic layer was dried. The aqueous layer was extracted with 50 mL of ethyl acetate; the extract was dried and combined with the original organic layer. The combined organic layers were concentrated in vacuo. Flash chromatography on 100 g of silica gel using 9:1 v/v CH$_2$Cl$_2$/ethyl acetate, then 4:1:0.1 v/v/v CH$_2$Cl$_2$/ethyl acetate/acetic acid as the eluant afforded 1.03 g (86%) of 1: [α]=+68.3.

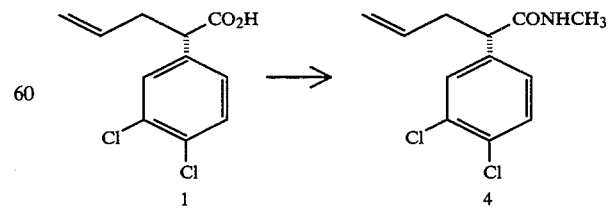

N-Methyl (2S)-(3,4-Dichlorophenyl)-4-pentenamide (4). A solution of 3.50 g (14.3 mmol) of 1 and 5 mL of oxalyl chloride in 40 mL of CH$_2$Cl$_2$ was treated with 0.1 mL of DMF. Gas evolution was observed. The resulting mixture was stirred at rt for 45 min and concentrated in vacuo.

A solution of the crude acid chloride in 15 mL of toluene was slowly added to a cooled (0° C.), rapidly stirring mixture of 30 mL of toluene and 10 mL of 40% aqueous methylamine solution. The cooling bath was removed and the mixture was stirred for 30 min. The reaction mixture was diluted with 50 mL of ethyl acetate and 20 mL of water and the layers were separated. The organic layer was washed with 2 ×25 mL of 2.0 N HCl, 25 mL of sat'd NaHCO₃, 25 mL of sat'd NaCl, dried and concentrated in vacuo. The resulting solid was recrystallized from 200 mL of 10:1 v/v hexanes/ethyl ether to afford 3.22 g of 4. The crystallization liquor was concentrated in vacuo. Flash chromatography on 20 g of silica gel using 3:2 v/v hexanes/ethyl ether as the eluant afforded 0.35 g of 4 (97% total yield) as a solid, mp=104°-105° C.: $[\alpha] = +73.4$ (c=0.9, CHCl₃), ¹H NMR 2.44–2.50 (m, 1H), 2.78 (d, 3H, J=4.8), 2.81–2.90 (m, 1H), 3.31 (t, 1H, J=7.2), 5.01 (d, 1H, J=16.8), 5.05 (d, 1H, J=24.0), 5.48 (br s, 1H), 5.61–5.72 (m, 1H), 7.18 (dd, 1 H, J=8.0, 2.6), 7.39–7.42 (m, 2H); FAB-MS 259(M+1)⁺. Anal. Calcd for C₁₂H₁₃Cl₂NO: C, 55.83; H, 5.07; N, 5.43; Cl, 27.47. Found: C, 55.80; H, 5.03; N, 5.40; Cl, 27.29.

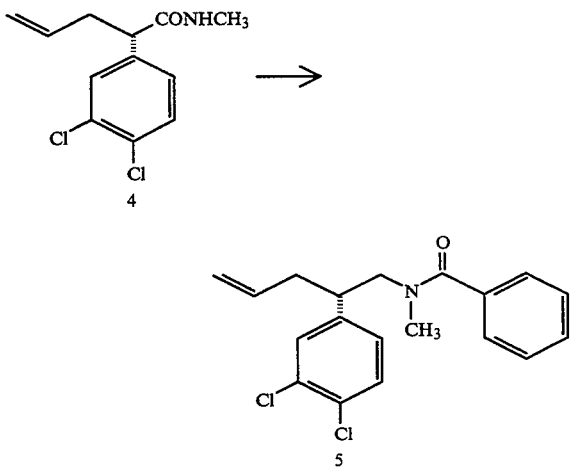

N-Methyl-N-((2S)-(3,4-dichlorophenyl)-4pentenyl) benzamide (5). A solution of 775 mg (2.6 mmol) of 4 in 6 mL of CH₂Cl₂ was slowly added to 7.0 mL of 1.5M diisobutylaluminum hydride solution in toluene at 0° C. The cooling bath was removed and the resulting solution was stirred at rt for 16 h. The reaction was carefully quenched with 20 mL of 2.0 N NaOH and extracted with 50 mL of ethyl ether. The organic layer was separated, washed with 15 mL of sat'd NaCl and dried. The aqueous layers were combined and extracted with 2×25 mL of ethyl ether; each extract was dried and combined with original organic layer. The combined organic layers were concentrated in vacuo. The crude amine was filtered through a pad of 35 g of silica gel using 50:1:0.1 v/v/v CH₂Cl₂/CH₃OH/NH₄OH as the eluant to afford 553 mg (76%) of pure amine:

¹H NMR 1.42 (br s, 1H), 2.25–2.32 (m, 1H), 2.37–2.44 (m, 1H), 2.38 (s, 3H), 2.73–2.86 (m, 3H), 4.95–5.01 (m, 2H), 5.48–5.72 (m, 1H), 7.04 (dd, 1H, J=8.4, 2.0), 7.29 (d, 1H, J=2.0), 7.38 (d, 1H, J=8.4).

A mixture of 550 mg (1.96 mmol) of the aforementioned amine, 10 mL of toluene and 10 mL of sat'd NaHCO₃ at 0 ° C. was treated with 0.60 mL (5.0 mmol) of benzoyl chloride. The cooling bath was removed and the mixture was stirred for 1 h. The mixture was diluted with 75 mL of ethyl ether and the layers were separated. The organic layer was washed with 25 mL of 2.0 N HCl, 25 mL of 2.0 N NaOH, 25 mL of sat'd NaCl, dried and concentrated in vacuo. Flash chromatography on 35 g of silica gel using 2:1 v/vhexanes/ethyl ether as the eluant afforded 734 mg (97%) of 5 as an oil: $[\alpha] = -38.6$ (c=1.4, CHCl₃);

¹H NMR (2:1 mixture of amide rotamers), major rotamer: 2.41–2.49 (m, 2H), 2.69 (s, 3H), 3.24–3.27 (m, 1H), 3.55–3.60 (m, 2H)4.98–5.06 (m, 2H), 5.63–5.73 (m, 1H). Minor rotamer: 2.15–2.23 (m, 2H), 2.86–2.89 (m, 1H), 3.03 (s, 3H) 3.50–3.55 (m, 1H), 3.86–3.91 (m, 1H). For both rotamers: 6.78 (app s), 6.91 (app s), 7.06 (app s), 7.14–7.43 (m); IR (neat) 1632, 1472, 1400, 1070, 1028, 992, 916; FAB-MS 349(M+1)⁺.

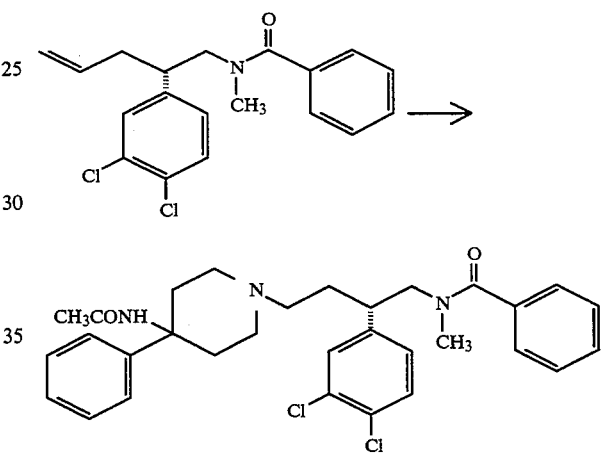

N-Methyl-N-((2S)-(3,4-dichlorophenyl)-4-(4-acetamido-4-phenylpiperidinyl)butyl benzamide (7, SR 48968). A solution of 1.30 g (3.7 mmol) of 5 in 16 mL of 2:1:1 v/v/v acetone/t-butanol/water was treated with 13 mg (0.05 mmol) of osmium tetroxide. After 5 min, 676 mg (5.5 mmol) of N-methylmorpholine N-oxide was added and the resulting mixture was stirred at rt for 1 h. The reaction was quenched with approximately 500 mg of sodium bisulfite and concentrated in vacuo to 25% of the original volume. The residue was partitioned between 75 mL of CH₂Cl₂ and 25 mL of water and the layers were separated. The organic layer was dried. The aqueous layer was extracted with 2×25 mL of CH₂Cl₂; each extract was dried and combined with the original organic layer. The combined organic layers were concentrated in vacuo to afford the crude diol.

A solution of the diol in 20 mL of 3:1 v/v THF/water was treated with 1.40 g (6.5 mmol) of sodium periodate. After 20 min, the reaction mixture was partitioned between 75 mL of ethyl ether and 25 mL of water and the layers were separated. The organic layer was dried. The aqueous layer was extracted with 50 mL of ethyl ether; the extract was dried and combined with the original organic layer. The combined organic layers were concentrated in vacuo. The residue was filtered through a pad of 60 g of silica gel using ethyl ether as the eluant to afford 944 mg (72%) of aldehyde 6.

A solution of 710 mg (2.0 mmol) of aldehyde 6 and 750 mg (2.9 mmol) of 4-acetamido-4-phenylpiperidine HCl in 15 mL of methanol at 0 ° C. was treated with 6.0 mL of 1 $\underline{M}$ sodium cyanoborohydride solution in THF. The cooling bath was removed and the mixture was stirred at rt for 16 h. .The reaction was quenched with 10 mL of sat'd $NaHCO_3$ and concentrated in vacuo to 50% of the original volume. The residue was partitioned between 75 mL of ethyl acetate and 15 mL of water and the layers were separated. The organic layer was dried. The aqueous layer was extracted with 50 mL of ethyl acetate; the extract was dried and combined with the original organic layer. The combined organic layers were concentrated in vacuo. Flash chromatography on 50 g of silica gel using 20:1 v/v $CH_2Cl_2$/methanol as the eluant afforded 981 mg (88%) of 5 as a foam: $[\alpha] = -21.6$ (c=0.7, $CHCl_3$); $^{13}C$ NMR (major amide rotamer only) 24.1, 28.9, 33.7, 33.8, 39.0, 41.0, 49.3, 49.6, 53.2, 55.6, 57.0 124.9, 126. 5, 127.1, 127.3, 128.5, 128.6, 129.8, 130.1, 130.9, 131.1, 131.3, 132.7, 135.9, 141.6, 144.5, 170.5, 172.0; FAB-MS 553(M+1)+.

What is claimed is:

1. An activated ester of the compound of formula 1,

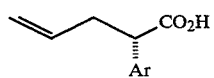

wherein:

Ar is:

aryl wherein the aryl is selected from the group
(1) naphthyl,
(2) phenyl,
(3) pyridyl,
(4) furyl,
(5) thienyl,
(6) thiazolyl,
(7) isothiazolyl,
(8) imidazolyl,
(9) benzimidazolyl,
(10) pyrazinyl,
(11) pyrimidyl,
(12) quinolyl,
(13) isoquinolyl,
(14) benzofuryl,
(15) benzothienyl,
(16) pyrazolyl,
(17) indolyl,
(18) purinyl,
(19) isoxazolyl, wherein the aryl is substituted with
(1) halogen,
(2) $C_{1-3}$alkyl,
(3) trifluoromethyl,
(4) $C_{1-3}$alkoxy,
(5) hydroxy, or
(6) methylenedioxy, wherein the activated ester is formed by treating said compound of formula 1 with dicyclohexylcarbodiimide and 1-hydroxybenzotriazole or formed by treating said compound of formula 1 with 1-(3-dimethyl-aminopropyl)-3-ethylcarbodiimide hydrochloride.

2. A compound which is (2S)-(3,4-Dichlorophenyl)-4-pentenoic acid.

* * * * *